United States Patent [19]

Alapati et al.

[11] Patent Number: 5,663,492
[45] Date of Patent: Sep. 2, 1997

[54] SYSTEM FOR CONTINUOUS ANALYSIS AND MODIFICATION OF CHARACTERISTICS OF A LIQUID HYDROCARBON STREAM

[76] Inventors: Rama Rao Alapati, 200 Oakcrest Dr., Apartment #275, Lafayette, La. 70503; Bryan H. Sonnier, 111 Marla Dr.; Houman M. Shammai, 411 Robinhood Cir., both of Lafayette, La. 70508

[21] Appl. No.: 658,640

[22] Filed: Jun. 5, 1996

[51] Int. Cl.$^6$ ............................................. G01N 7/00
[52] U.S. Cl. .................. 73/64.45; 73/61.59; 73/19.01; 203/2
[58] Field of Search ............................ 73/19.01, 19.1, 73/19.12, 23.41, 61.41, 61.43, 61.59, 64.45, 863.12, 864.83, 864.84; 203/2

[56] References Cited

U.S. PATENT DOCUMENTS

| | | | |
|---|---|---|---|
| 4,252,614 | 2/1981 | Stewart | 203/2 X |
| 4,298,363 | 11/1981 | Campbell | 203/2 X |
| 4,328,073 | 5/1982 | Likins | 203/2 |
| 4,332,159 | 6/1982 | Chin et al. | 73/64.45 |
| 4,555,309 | 11/1985 | Jain | 203/2 X |
| 4,558,423 | 12/1985 | Jain | 203/2 X |
| 4,667,508 | 5/1987 | Soderstrom et al. | 73/64.45 |
| 4,783,989 | 11/1988 | Reed | 73/64.45 |
| 4,894,145 | 1/1990 | Jensen | 203/2 X |
| 5,047,125 | 9/1991 | Meier et al. | 73/64.45 X |
| 5,132,918 | 7/1992 | Funk | 203/2 X |
| 5,162,081 | 11/1992 | Bowes | 203/2 |
| 5,172,586 | 12/1992 | Reed | 73/64.45 |
| 5,191,786 | 3/1993 | Baughman et al. | 73/64.45 |
| 5,222,032 | 6/1993 | Fleming | 73/19.1 |
| 5,390,551 | 2/1995 | Carvahak et al. | 73/19.01 |
| 5,499,531 | 3/1996 | Henderson | 73/64.45 |

*Primary Examiner*—Hezron E. Williams
*Assistant Examiner*—Jay I. Politzer
*Attorney, Agent, or Firm*—Jesse D. Lambert

[57] ABSTRACT

Apparatus and method for continuous analysis and/or modification of the vapor pressure characteristics of a hydrocarbon stream includes: liquid/gas separation chamber; constant flow liquid influent means; liquid level sensing means; temperature control means; constant pressure gaseous effluent means; liquid effluent means having a flow rate responsive to liquid level sensing means; and influent and effluent flow metering means. Means for sensing composition of gaseous effluent, and manifold means responsive to said composition for variable blending of differing liquid hydrocarbon streams, may also be provided. Influent may be heated or cooled prior to entering the separation chamber.

In the preferred embodiment, liquid influent rate is substantially constant. Temperature and pressure, which pressure may be made sub-atmospheric by vacuum means, are selected and maintained. In the separation chamber, components of the liquid influent having vapor pressures above the selected temperature and pressure of the separation chamber are volatized. Diffusion and mixing means in the chamber enhance rapid volatilization. Separated gas is flowed from the chamber and its composition analyzed by chromatography means. Effluent liquid is flowed from the chamber at a rate which maintains a constant liquid level in the chamber. By measurement and/or control of blending of influent streams, pressure, and/or temperature of the separation chamber responsive to vapor characteristics of liquid effluent, a stream of liquid hydrocarbons may be continuously analyzed and a liquid effluent having desired vapor pressure characteristics continuously produced and/or verified.

16 Claims, 1 Drawing Sheet

SYSTEM FOR CONTINUOUS ANALYSIS AND MODIFICATION OF CHARACTERISTICS OF A LIQUID HYDROCARBON STREAM

BACKGROUND OF THE INVENTION

1. Field of the Invention

Naturally occurring liquid hydrocarbons, such as crude petroleum, are typically a complex composition of many individual organic chemicals of differing molecular length, weight and form. Some of these organic chemicals are quite volatile, with some of the volatile organic chemicals of special environmental concern. For instance benzene, toluene, ethyl benzene and xylene are strictly regulated in the United States. As the existence of personnel and environmental hazards, the cost of mitigating said hazards, and other important characteristics of a liquid hydrocarbon depend fundamentally on whether a liquid hydrocarbon emits vapors at a given pressure and temperature, the accurate determination of the vapor pressure of a liquid is of key importance. Of equal importance is the capability to modify the measured vapor pressure to bring a liquid hydrocarbon within desired or mandated vapor pressure, and possibly vapor composition, conditions.

In addition to compliance with regulatory requirements regarding vapor characteristics, or achieving specified vapor characteristics for processing purposes (as in refinery applications), the ability to do so in an economically optimum manner is important. Such regulatory and operational requirements may be achieved by controlled blending of multiple liquid hydrocarbon streams of different vapor characteristics and unit costs, to yield a blended liquid representing the optimum combination of vapor characteristics and unit costs.

The present invention relates generally to apparatus and methods for continuous determination of the amount and volatility of hydrocarbon compounds contained in a liquid hydrocarbon stream. The present invention also relates to apparatus and method for continuous, real-time modification of the vapor characteristics of a liquid hydrocarbon stream, responsive to measured characteristics of the stream, so that excessive amounts of undesirable VOCs ("Volatile Organic Compounds") may be removed from the liquid before exposure to atmospheric conditions. In addition, oil shrinkage (effluent volume as compared to influent volume) and gas/oil ratio (GOR) may be determined with the apparatus. Therefore, the present invention relates to the field of continuous direct analysis of an influent stream of liquid hydrocarbons and, as required, modification (responsive to said analysis) of the composition of said stream, for production of an effluent stream of liquid hydrocarbons having desirable vapor characteristics. In addition, means for identifying the volatile components of the liquid hydrocarbon stream may be provided.

2. Description of the Related Art

Many liquid hydrocarbons, particularly those naturally occurring such as liquid crude oil, are a complex admixture of many hydrocarbon compounds of differing molecular length, weight and/or molecular geometry. Those hydrocarbon compounds typically vary, for instance in naturally occurring crude oil, from compounds having a low molecular weight, such as methane (having one carbon atom) to compounds having many carbon atoms and a relatively high molecular weight, such as various asphalt molecules. Those compounds in the lower range of molecular weights are commonly referred to as the "light ends", while those in the upper range of molecular weights are commonly called the "heavy ends". While in pure form the vapor pressure curve (a pressure versus temperature curve defining a line of pressures and corresponding temperatures at which liquid to gas and gas to liquid transfer is in equilibrium) of each of these individual compounds is generally well known, in field application the vapor pressure characteristics of a complex admixture are not readily predictable because of two factors. First, in complex admixture, many of the individual components interact chemically and physically, modifying what might be expected to be a particular compound's partial pressure contribution to the total vapor pressure of the complex admixture. Secondly, precise analysis of the exact chemical and physical structure and amount of each component in a complex admixture is generally cost prohibitive, time consuming, includes various inaccuracies (as separation of the components for detailed analysis can change the components and their interaction with each other) and is of limited temporal utility. Further, it is ordinarily not necessary to know the precise composition and amount of every component of crude liquid petroleum at every point in time to establish the value or utility of the liquid petroleum.

However, because of exigent environmental and safety concerns, there is a need for greater information about and control of the vapor characteristics of liquid hydrocarbons. Due to the massive quantities of crude oil production worldwide significant environmental concerns have arisen, and will likely continue to arise, from emissions of VOC vapors therefrom. Of special environmental concern are certain compounds believed to be hazardous, commonly referred to as "BTEX" (benzene, toluene, ethyl benzene and xylene). For instance, the 1990 Clean Air Amendments establish as major sources of air pollution any facility which emits more than a specified annual quantity of any one or a combination of hazardous pollutants and require control of such emissions.

Significant other concerns also arise from the volatile components of liquid hydrocarbons in their storage and processing. All of said VOCs are at least inflammable or explosive in certain concentrations, posing acute safety hazards in enclosed conditions. In pumping operations gas bubbles within the liquid stream can occur under certain pressure and temperature conditions, affecting pump operation and system safety. The volatile components of crude liquid petroleum can affect its value in several respects; such components indicate how much liquid "shrinkage" may occur in storage, what kind of storage facility may be required, and the expenses that may have to be incurred to prevent excessive emissions. Additionally, the chemical and/or physical characteristics of vapor quantity and content frequently affect the usability of the liquid hydrocarbon admixture for certain purposes, the nature and expense of processing which may be required to produce desired products, the risks to personnel and to the environment attendant to handling or use of the admixture, and many similar concerns. For these reasons, it is desired to have a means for continuously, precisely, and accurately analyzing through direct measurement and, if necessary, modifying the quantity and/or character of the volatile components of a liquid hydrocarbon flowstream, under dynamic conditions, the modifications being performed responsive to said analysis.

The necessary analysis poses several problems. For example, current empirical methods of vapor pressure determination are often substantially in error when compared to more accurate measurements done under controlled, static conditions in a laboratory, such as in static pressure-volumetemperature (PVT) cells. One such empirical method is the Reid Vapor Pressure Test according to ASTM D-323-90. The Reid method involves collecting a sample of the liquid hydrocarbon at atmospheric pressure, chilling the sample, combining the liquid hydrocarbon sample with an air volume at 100° F., then agitating the combined air volume and liquid hydrocarbon sample until the pressure equalizes. The resulting pressure is then reported as the Reid Vapor Pressure.

It has long been recognized that Reid Vapor Pressure values may be greatly in error. Efforts to improve the accuracy of the Reid Vapor Pressure test have generated "correction" procedures such as that outlined in API 2517. The API 2517 procedure utilizes a nomograph in an effort to generate a "true" vapor pressure from the Reid vapor pressure value and the actual stock tank liquid hydrocarbon temperature. However, laboratory tests have shown that even the API 2517 value is often in error.

Static laboratory-type PVT measurements are not practical for field testing of large liquid hydrocarbon volumes due to the lengthy test time required and the relatively small sample volume tested. Further, such static PVT cell apparatus are of a relatively fragile nature, not readily compatible with field usage.

Spicar, U.S. Pat. No. 5,339,672 (Aug. 23, 1994) discloses an apparatus for monitoring hydrogen gas present in electrical transformer oil. A cell has a glass filter within, disposed a distance from the top of the cell, the glass filter having small pores therethrough. Transformer oil is flowed into the upper oil compartment between the glass filter and the top of the cell. Oil flows through the glass filter under pressure and then to the bottom of the cell where a lower gas and liquid space are formed. Lower liquid level is controlled by a liquid effluent pump. Gas from the gas space (driven by an induced temperature differential) flows through a hot wire gas detector which detects the concentration of hydrogen in the gas. No means is disclosed for determining the quantity and composition of organic vapors at controlled temperatures and pressures and modifying the vapor characteristics of the liquid as desired.

Fleming, U.S. Pat. No. 5,222,032 (Jun. 22, 1993) is directed to apparatus and method for determining the amount of organic chemicals, such as carbon tetrachloride, in a liquid wastestream, such as water. Wastewater is injected into a vessel at a sufficient velocity to create bubbles and turbulence in a vessel. The turbulence is said to enhance breakout of gases entrained in the liquid. A stripper gas may also be injected into the liquid to enhance gas breakout. The quantity of undesirable gases is then measured as a function of time, determining the response time of the system. No means, responsive to effluent characteristics, is disclosed for control of temperature and pressure of the vessel, or for blending of multiple influent streams of differing characteristics.

Other apparatus, such as those disclosed in Kanba, et al, U.S. Pat. No. 5,062,292 (Nov. 5, 1991) and Baughman, et al, U.S. Pat. No. 5,191,786 (Mar. 9, 1993), determine gas dissolved in batch oil samples by injecting "stripper" gas into the oil (which may be diluted) and then analyzing the combined stripper gas/extracted gas sample.

Henderson, U.S. Pat. No. 5,499,531 (Mar. 19, 1996) discloses a system and method for calculating the composition of a liquid hydrocarbon using an iterative mathematical algorithm. From the calculated composition of the liquid hydrocarbon, the partial pressure of each hydrocarbon compound therein may be calculated and aggregated to produce a calculated total vapor pressure. Henderson addresses direct liquid vapor pressure determination only as a "check" method on the iterative liquid composition calculation/partial pressure method. The apparatus and method allegedly invented by Henderson and set forth in U.S. Pat. No. 5,499,531 discloses no pressure control means by which separation chamber pressure may be sustained at sub-atmospheric values as well as above atmospheric values for continuous liquid vapor characteristic modification and direct measurement thereof. In Henderson, temperature control of the liquid influent is limited to maintaining temperature only high enough to evolve some vapor therefrom for gas composition analysis; further, said temperature control is performed only by means external to the vessel, and no diffusion means within the vessel is disclosed. Further, Henderson discloses no means by which multiple liquid hydrocarbon streams may be blended to yield a composite liquid hydrocarbon influent having desired vapor characteristics.

None of these patents disclose the present invention. The related art shows no apparatus or method which provides a direct, continuous measurement of the vapor characteristics of a hydrocarbon stream at pressures controlled below or above atmospheric pressure, at a selected temperature. Further, no apparatus is shown which is capable of modifying the vapor characteristics of a liquid hydrocarbon influent stream by pressure and temperature control and blending, responsive to effluent characteristics, to produce a liquid hydrocarbon effluent having desired vapor characteristics at pressures below and above atmospheric. The apparatus of the present invention provides an accurate, field-compatible means for measurement and modification of the vapor characteristics of a hydrocarbon stream.

A general object of the present invention is to provide improved apparatus and method for measuring the vapor characteristics of a stream of liquid hydrocarbons, such as liquid petroleum. Another general object of the present invention is to provide improved apparatus and method to modify the vapor characteristics of an influent liquid hydrocarbon stream so as to produce an effluent liquid hydrocarbon stream having desired vapor characteristics.

With more particularity, other objects of the present invention are to provide transportable apparatus adaptable to field use; to provide methods which are simple to follow; to provide apparatus and methods for direct, continuous measurement of total vapor pressure of a flowing stream of liquid hydrocarbons; to provide means for measurement of the vapor pressure of hydrocarbons with increased accuracy; to provide apparatus and methods for modification of the vapor characteristics of a hydrocarbon stream; to provide apparatus and methods having a plurality of means for modification and control of the vapor pressure characteristics of a hydrocarbon stream; to provide apparatus and methods for determining liquid hydrocarbon shrinkage and GOR; and to provide apparatus and methods wherein blending of influent streams and/or temperature and/or pressure at which liquid/gas separation occurs may be varied, in real time, responsive to measurement of effluent characteristics, to produce a liquid effluent of desired characteristics. Yet another object is to perform such modifications with an optimum expenditure of energy, by using a combination of pressure control, temperature control, and blending.

SUMMARY OF THE INVENTION

The system for continuous analysis and/or modification of characteristics of a liquid hydrocarbon stream is characterized by a liquid/gas separation chamber having temperature control means and liquid level sensing means; a substantially constant flow liquid influent means for maintaining a desired rate of flow of liquid hydrocarbons into said separation chamber; liquid effluent means, comprising a liquid effluent line having an effluent pump controlled by said liquid level sensing means; constant pressure gaseous effluent means comprising a gas effluent line, a pressure sensing means and pressure control means.

The influent stream of liquid hydrocarbons may be drawn from manifold means wherein several streams of hydrocarbon, each potentially having differing vapor characteristics, are blended. Blending may be controlled by measured characteristics of the liquid effluent stream. An influent pump supplies liquid hydrocarbon to the separation chamber at a selectable, preferably constant rate of flow, pumping through a liquid influent line and orifice means. The pressure in said liquid influent line is maintained substantially above the separation chamber pressure. Temperature of the influent may be adjusted by various heating and/or cooling means. The liquid/gas separation chamber has a liquid level sensing means, a temperature control means comprising a temperature sensor and a heating element, and a pressure sensor. The liquid level sensing means in the separation chamber sends a signal to a microprocessor which controls the output of a liquid effluent pump which is attached to a liquid effluent line at the bottom of the liquid/gas separation chamber. Temperature control means controls separation chamber temperature. The liquid/gas separation chamber may be insulated to facilitate temperature control. Mixing means disposed within the separation chamber maintains uniformity of the liquid hydrocarbon therein and aids liquid/gas separation. Diffusion means disposed within the separation chamber distributes liquid influent across the separation chamber and provides increased gas/liquid contact area. Pressure of the liquid/gas separation chamber is controlled by pressure control means which may be disposed on the gas effluent line or on a separate line, said pressure control means responsive to said pressure sensor means. The pressure control means comprises vacuum means and pressure regulator means, so that separation chamber pressure may be maintained below or above atmospheric pressure. Flow rates of liquid influent and liquid and gaseous effluents are measured by influent and effluent flow metering means.

In use the total vapor pressure of the liquid hydrocarbon stream may be directly measured by first reducing separation chamber pressure using the pressure control means to a pressure (which may be sub-atmospheric) below the expected vapor pressure of the liquid. The liquid hydrocarbon stream is then flowed through the liquid/gas separation chamber at a constant temperature, while maintaining constant liquid level in the liquid/gas separation chamber, with the pressure control means on the gas effluent line closed. As the liquid hydrocarbon enters the separation chamber, the higher vapor pressure components will "flash off" or vaporize since the separation chamber pressure is below the liquid's vapor pressure. The pressure within the liquid/gas separation chamber will increase and equalize at a pressure which is by definition the total vapor pressure of the liquid hydrocarbon at the constant temperature. The total vapor pressure measurement may be repeated at different temperatures to define a vapor pressure curve. If desired, analysis of the composition of the vapors may be accomplished by an analytical instrument, such as a gas chromatograph, connected to the gas effluent line.

The vapor characteristics of liquid hydrocarbons may be continuously modified by controlling separation chamber pressure at the desired vapor pressure, while flowing liquid hydrocarbon through the separation chamber at constant temperature and liquid level. By permitting gas effluent flow from the chamber while maintaining the desired back pressure (whether below or above atmospheric pressure) on the separation chamber, the resulting liquid effluent will have a total vapor pressure equal (whether below or above atmospheric pressure) to the separation chamber pressure. Liquid shrinkage and GOR may be determined by comparison of rate data from the influent and effluent flow metering means.

A microprocessor receives temperature, pressure, liquid rate, liquid level, and gas rate and may be used to record data and to control blending, temperature or pressure of the processing of a stream of liquid hydrocarbons, to produce a liquid effluent having desired characteristics.

DESCRIPTION OF THE PREFERRED EMBODIMENT

Figure 1:
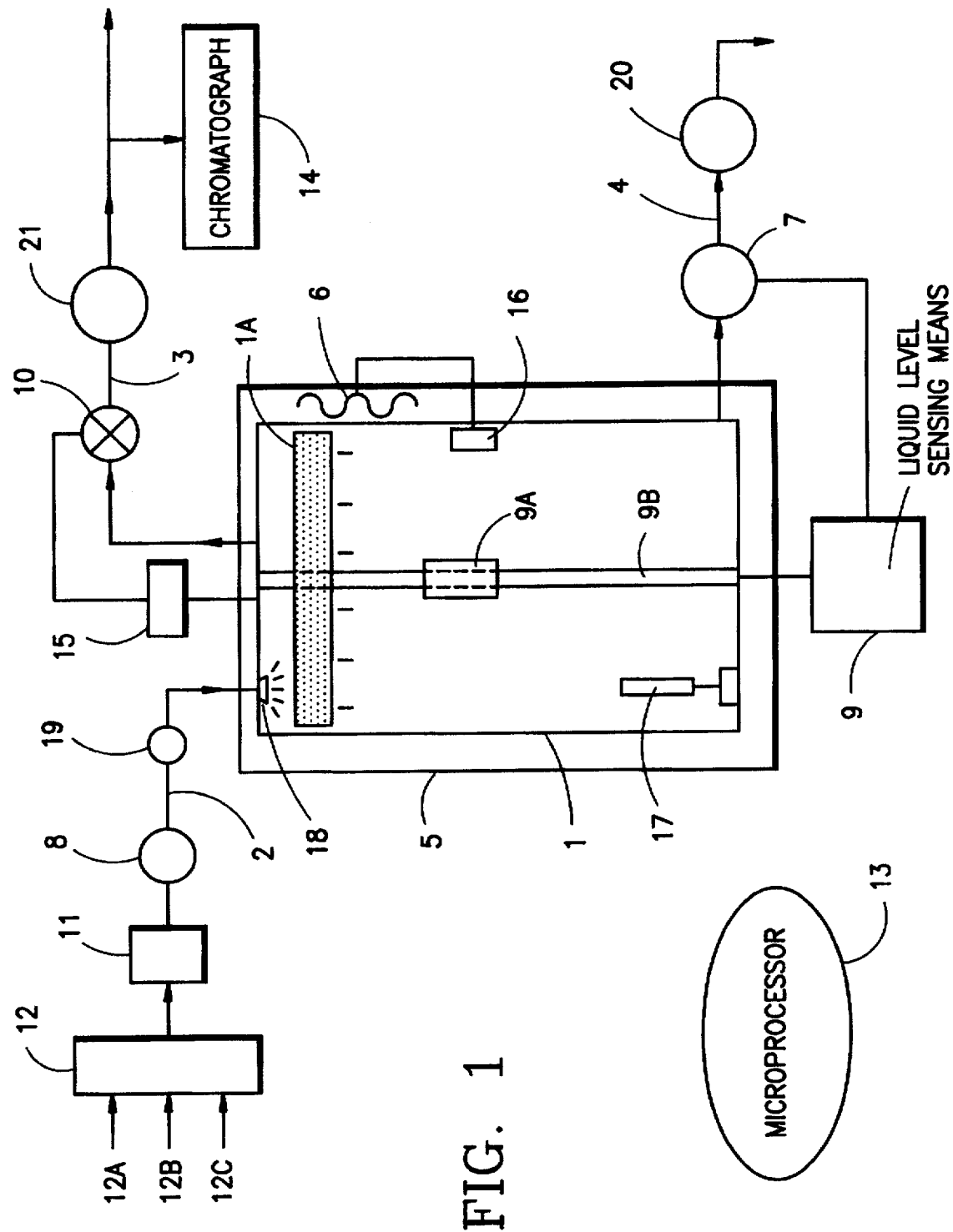
FIG. 1 is a schematic of the apparatus of the present invention, showing the various components of the preferred embodiment of the present invention as described below.

With reference to FIG. 1, separation of liquid and gaseous components of a liquid hydrocarbon stream occurs in separation chamber 1. Separation chamber 1 is preferably made of a material which is compatible with hydrocarbons at pressures below and above atmospheric and temperatures in the range of 200° F. Inside separation chamber 1 diffusion means 1A of permeable steel mesh or other suitable material may be provided to distribute liquid hydrocarbon influent and provide a larger surface area for gas/liquid interface, and thus exchange, to occur.

Separation chamber 1 is maintained at a constant, selectable temperature, by temperature control means comprising temperature sensor 16 and heating element 6. Temperature sensor 16 may include any number of well known temperature sensors, such as thermocouples, gas and/or liquid filled expansion systems, bi-metallic systems etc. Heating element 6 may include any number of well known heating means, including electrical resistance heaters, heated gas or liquid circulating through coils, etc. Separation chamber 1 is preferably contained within insulating enclosure 5 to facilitate temperature control of the chamber.

Separation chamber 1 has a liquid level sensing means 9, which in the preferred embodiment includes float system (float 9A slidably disposed on rod 9B). Rod 9B is hollow and contains a magnetic sensor means therein which detects the position of the metal float 9A on the exterior of rod 9B and produces an electrical signal representing liquid level. Other liquid level sensing means well known in the art could be used. In the preferred embodiment the electrical signal of liquid level sensing means 9 is fed into a microprocessor 13 which controls liquid effluent pump 7, pumping liquid out of separation chamber 1 through liquid effluent line 4. While different liquid levels can be selected, once selected microprocessor 13 controls the output of liquid effluent pump 7 so as to maintain a constant liquid level in separation chamber 1. A variety of other well known means could be used to control liquid effluent rate responsive to liquid level in separation chamber 1. Mixing means 17 within separation chamber 1 ensures a homogenous liquid therein and aids liquid/gas separation. Mixing means 17 may be a rotating, paddle type mixer or other mixing means well known in the art.

Influent of liquid hydrocarbon into separation chamber 1, in the preferred embodiment, is provided by constant flow liquid influent means comprising liquid influent line 2 and liquid influent pump 8, which maintains a selected pressure on orifice 18, thereby maintaining a substantially constant rate of flow of liquid influent into separation chamber 1 through liquid influent line 2. Pressure upstream of orifice 18 is maintained sufficiently high to ensure that the liquid influent remains in single phase flow and to prevent separation chamber pressure fluctuations from influencing influent rate. By way of example, pressure upstream of the orifice may be maintained at approximately 200 psi. Other constant flow control means could be used, such as gravity feed or a pump combined with pressure regulator means. The preferred embodiment supplies substantially constant rate liquid influent to minimize liquid level fluctuations, avoid liquid level sensing and control means modulation, and increase level control accuracy. However, some variation in influent rate may exist. Manifold means 12 is capable of receiving multiple liquid hydrocarbon flow streams, characterized by lines 12A, 12B and 12C, so as to create a desired blend of liquid hydrocarbon into liquid inherent line 2. It is understood that although three lines are shown feeding manifold means 12, the number is by way of illustration only, and any number of lines could be so used. Influent temperature adjusting means 11 may also be provided to either heat or cool the influent as desired. In the preferred embodiment influent is injected into separation chamber 1 at a temperature equal to the separation chamber temperature, to minimize temperature disturbances within the chamber. Cooling is accomplished by air exchanger, if required, and heating is accomplished by heated water or glycol exchanger, if required. Any other well known heating or cooling means could also be used.

Volume of liquid in separation chamber 1 being maintained constant by constant rate of influent (as aforesaid) and variable rate of liquid effluent responsive to liquid level control system (as aforesaid), and temperature of separation chamber 1 being maintained constant by temperature control means (as aforesaid), only pressure remains variable to define the vapor pressure characteristics of a stream of liquid hydrocarbons. The pressure at which liquid/gas separation occurs in separation chamber 1 is determined by pressure control means coupled to said separation chamber 1. In the preferred embodiment, pressure control means 10 comprises vacuum means (for controlling separation chamber pressure below atmospheric) and pressure regulator means (for controlling separation chamber pressure above atmospheric) attached to gas effluent line 3 to produce desired pressures in separation chamber 1. Said vacuum means may comprise a vacuum pump or similar vacuum source. Said pressure regulator means may comprise a flow control means such as a valve or other means for maintaining a pressure greater than atmospheric. However, other embodiments could include the pressure control means 10 coupled to separation chamber 1 by a line separate from gas effluent line 3.

To analyze a liquid hydrocarbon, at least one liquid hydrocarbon stream is flowed into manifold means 12 and through influent line 2, passing through influent temperature adjusting means 11. Influent pump 8 provides a selectable pressure (which is substantially higher than the pressure in separation chamber 1) which operates in conjunction with orifice 18 to maintain a substantially constant flow rate of liquid hydrocarbon into separation chamber 1. Liquid hydrocarbon influent entering separation chamber 1 separates into liquid and gaseous components by virtue of lowering of influent pressure as it enters separation chamber 1, with separation aided by diffusion means 1A which provides a large area for liquid/gas exchange to occur, and by mixing means 17. Liquid level sensing means 9 within separation chamber 1 continuously senses the liquid level therein and sends an electrical signal to microprocessor 13, which adjusts the flow rate through liquid effluent pump 7, increasing or decreasing the rate as necessary, so as to maintain a selected constant liquid hydrocarbon level within separation chamber 1.

To measure the true total vapor pressure of a liquid hydrocarbon, the separation chamber pressure is initially brought to a pressure below the expected vapor pressure of the liquid. The pressure should be lower than the expected vapor pressure of the liquid to be measured to provide an environment wherein the higher vapor pressure components of the liquid hydrocarbon will vaporize upon entering the separation chamber. Typically, the initial pressure will be established as sub-atmospheric with the vacuum means of pressure control means 10. Temperature of separation chamber 1 is selected and maintained at a constant desired level. Liquid influent temperature is adjusted using influent temperature adjusting means 11 to equal separation chamber 1 temperature. Influent is flowed into and out of separation chamber 1 while maintaining constant liquid level via level sensing means 9 and effluent pump 7. With pressure control means 10 on gas effluent line 3 closed so that no gas flows from the separation chamber, the separation chamber pressure will build to the true vapor pressure, measurable by pressure sensor 15. In effect, the constant temperature, constant liquid level of separation chamber 1, while flowing liquid hydrocarbon therethrough, creates a continuous flow-through pressure-volume-temperature (PVT) cell, with which the vapor pressure can be directly and continuously measured with high accuracy. The vapor pressure thus obtained is indicative of the total vapor quantity from the liquid, at the test temperature measured by temperature sensor 16.

The total vapor pressure of a liquid hydrocarbon can also be determined by first adjusting separation chamber 1 pressure to a value below an expected vapor pressure as described above. The gas effluent line is closed, and the pressure control means is set to permit a maximum separation chamber 1 pressure greater than a maximum output pressure from said liquid influent supply means. Then, liquid hydrocarbon is flowed through separation chamber 1 while maintaining substantially constant temperature and liquid level therein. A recording (which may advantageously be done by plotting) is made of the separation chamber 1 pressure with time. Liquid hydrocarbon flow-through is continued with the resulting plot of separation chamber pressure versus time defining a function, and the asymptote to said function is by definition the total vapor pressure of the liquid hydrocarbon. The asymptote may be determined by visual means (using the plot) or by taking the derivative of the defined equation.

As is easily seen once the true vapor pressure of the liquid hydrocarbons and composition of the volatile components separated therefrom have been established at one temperature, temperature may be varied and the tests repeated, thereby defining a vapor pressure curve over a range of temperatures and also defining the composition of the volatile components which separate at various temperatures. From this data, precise required processing of the liquid hydrocarbons can be determined so as to produce a stream of liquid hydrocarbons which does not have volatile components which exceed regulatory requirements.

The apparatus of the present invention provides a means to produce a liquid hydrocarbon having a vapor pressure below or above atmospheric pressure, with vapor content within desired parameters. True vapor pressure may be first directly measured as described above, then appropriate modification implemented. To produce a liquid hydrocarbon having a desired vapor pressure and vapor content, the liquid is flowed into separation chamber 1 as described above, at a desired temperature. However, instead of closing gas effluent line 3 with pressure control means 10, gas flow is permitted at a rate sufficient to maintain separation chamber pressure at a constant desired value, with pressure control means 10 responsive to pressure sensor 15. Said gas flow and separation chamber 1 pressure may be below (by vacuum pump means) or above (by valve means) atmospheric pressure. By definition, the liquid effluent will have a vapor pressure equal to the constant back pressure maintained in the separation chamber 1, the back pressure as stated above being either below or above atmospheric pressure. Vapor composition may be continually analyzed by gas chromatograph 14 to ensure vapor composition within desired parameters. Influent and effluent rate data from liquid flow meters 19 and 20 permit determination of liquid shrinkage by dividing liquid effluent rate by liquid influent rate. Effluent flow rates from liquid effluent meter 20 and gas flow meter 21 permit determination of gas/oil ratios (GOR) by dividing gas effluent rate by liquid effluent rate, yielding gas/oil ratios typically expressed in cubic feet of gas per barrel of liquid hydrocarbon.

An alternate method to produce a liquid with a target vapor pressure/temperature combination is to use influent temperature adjusting means 11 and heating element 6 to bring liquid influent and separation chamber temperature to a value above the target temperature. Liquid is flowed through separation chamber 1, which is maintained with pressure control means 10 at a pressure greater than the target vapor pressure. A liquid effluent having a vapor pressure/temperature combination higher than the target values is thus produced. Upon cooling of the liquid effluent to the target temperature, the target vapor pressure will be as desired, either below or above atmospheric pressure. In effect, the increased temperature "boils off" certain of the higher vapor pressure hydrocarbon components, with the remaining components yielding a lower vapor pressure at the lower target temperature.

Yet another method of generating a liquid hydrocarbon having a target temperature/vapor pressure combination is to first directly measure the vapor pressure of the liquid hydrocarbon at its current temperature. Then, using means well known in the art, such as published chemical engineering relationships, the vapor pressure of the liquid when heated (or cooled, as may be) to the target temperature can be established. If the vapor pressure at the target temperature is too high, then the apparatus can be used to modify the vapor pressure at its current temperature to a vapor pressure value low enough to yield a desired vapor pressure at the target temperature. By such a procedure, the necessary vapor pressure modification may be effected at minimum energy expenditure.

In fact, appropriately sized, the apparatus of the present invention can be used to process a stream of liquid hydrocarbons to produce a liquid effluent which meets or exceeds all regulatory requirements. As is easily perceived, temperature at which separation occurs in separation chamber 1 can be increased to enhance volatilization of components. Pressure of the separation can be lowered to enhance volatilization of components and draw said components off from the liquid. By combination of high temperature and low pressure of separation virtually all of the undesirable volatile components of a liquid hydrocarbon can be permanently removed therefrom, leaving a liquid hydrocarbon which does not produce atmospheric pollution. As an added benefit many of the volatile components have substantial utility and value once separated from the hydrocarbon stream.

Blending means, comprising manifold means 12, permit multiple liquid hydrocarbon streams, each potentially having different vapor characteristics and unit costs, to be blended to yield a composite liquid having desired characteristics at lowest cost. By way of example, with multiple liquid streams available, the vapor characteristics of each stream can be directly measured as described above. Thereafter, with the vapor characteristics for each stream known, blending can be implemented at selected proportions and the vapor characteristics of the blended stream measured. Change of blending proportions, as needed, and measurement of the resulting vapor characteristics permits creation of a liquid effluent having the optimum combination of vapor characteristics and unit cost.

In the preferred embodiment a microprocessor 13 is used to receive electrical signals from the temperature, pressure and level sensors, to record temperature, pressure, and level data, and to produce control signals. For instance, microprocessor 13 controls the output of liquid effluent pump 7 to maintain constant liquid level in separation chamber 1. Microprocessor 13 may also be used to control blending of influent having different vapor characteristics (for instance some above and some below regulatory standards) so as to produce an effluent which is within regulatory standards. If measurement of the pressure and/or composition of the effluent were to indicate that the effluent was approaching regulatory limits the microprocessor 13 could automatically make appropriate adjustment of the valves admitting hydrocarbons to manifold 12 to assure a higher percentage of desirable hydrocarbons. Likewise microprocessor 13 could make appropriate adjustment of temperature and/or pressure at which liquid/gas separation occurs in separation chamber 1 to increase or decrease separation of volatile components from the liquid, so as to assure that the effluent has vapor characteristics meeting all regulatory requirements.

The present invention allows the operator to optimize energy requirements for modifying the liquid influent. Low separation chamber 1 temperatures may require energy to operate the vacuum pump means of pressure control means 10 to achieve a desired vapor pressure. Higher treating temperatures, while perhaps requiring no energy requirements for vacuum pump means operation, may require energy to raise the liquid influent to the desired treating temperature. The optimum balance between treating temperature and treating pressure minimizes the energy requirements to modify the influent.

The present invention also permits analysis of the effluent for confirmation of the vaporization characteristics by routing the effluent back through the apparatus for direct vapor pressure measurement and, if desired, gas composition measured by chromatograph 14. Alternatively, at least two of the apparatus may be used in series, with the first apparatus performing the modifications and the second apparatus confirming the vaporization measurements.

Many other embodiments of the present invention will be apparent to those skilled in the art, without departing from the spirit and intent of the invention, the full scope of which is intended to be comprehended by the following claims and the equivalents thereof.

We claim:

1. An apparatus for continuous measurement of the vapor pressure of a stream of liquid hydrocarbons, comprising:

a chamber having a lower portion substantially filled with hydrocarbons in liquid state and an upper portion substantially filled with vapors of said hydrocarbons, means for sensing the temperature of the hydrocarbons therein, means for sensing the level of liquid hydrocarbons therein, means for sensing the pressure of hydrocarbons therein, and, a heating element responsive to said temperature sensing means in thermal communication with the hydrocarbons in said chamber;

hydrocarbons influent line connected to a portion of said chamber which is above the level of liquid hydrocarbons therein;

hydrocarbons effluent line connected to a portion of said chamber which is below the level of liquid hydrocarbons therein;

hydrocarbons effluent pump responsive to said level sensing means for maintaining a constant level of liquid hydrocarbons in said chamber;

a vapor effluent line connected to a portion of said chamber which is above the level of liquid hydrocarbons therein; and, pressure control means in communication with a portion of the chamber which is above the level of liquid hydrocarbons in said chamber, said pressure control means responsive to the pressure of hydrocarbons in said chamber for maintaining said separation chamber at a selected pressure in a range below and above atmospheric pressure.

2. The apparatus of claim 1, wherein said pressure control means comprises a vacuum source and a valve, responsive to pressure of hydrocarbons in said chamber, in communication with said vaccuum source.

3. The apparatus of claim 2, further comprising liquid hydrocarbon diffusion means disposed within said chamber.

4. The apparatus of claim 3, wherein said hydrocarbon influent line further comprises a pump and an orifice disposed in said hydrocarbon influent line between said influent pump means and said separation chamber.

5. The apparatus of claim 4, further comprising a hydrocarbon flow meter disposed in said liquid influent line, a liquid flow meter disposed in said liquid effluent line, and a vapor flow meter disposed in said gas effluent line.

6. The apparatus of claim 5, wherein said pressure control means is disposed on said vapor effluent line.

7. The apparatus of claim 6, further comprising manifold means connected to said hydrocarbon influent line.

8. The apparatus of claim 7, further comprising influent temperature adjusting means disposed in said hydrocarbon influent line.

9. The apparatus of claim 8, further comprising means for continuously mixing of the liquid hydrocarbons in said chamber.

10. The apparatus of claim 9, further comprising vapor composition analysis means connected to said gas effluent line.

11. The apparatus of claim 10, wherein a microprocessor means receives data from said pressure sensing means, said level sensing means, said temperature sensing means, and said vapor composition analysis means, wherein said microprocessor processes said data to produce signals which control influent temperature, manifold means and pressure, level and temperature of hydrocarbons in said chamber so as to produce an effluent of liquid hydrocarbons having desired vapor pressure characteristics.

12. A method for continuous determination of the vapor pressure of a stream of liquid hydrocarbons, comprising the steps of:

a) providing an apparatus comprising:

a separation chamber having temperature sensor means, liquid level sensing means, and pressure sensor means therein, said separation chamber further having a heating element in thermal communication therewith, said heating element responsive to an output signal from said temperature sensor means;

selectable flow liquid influent means connected to a portion of said separation chamber which is above a liquid level in said separation chamber, said selectable flow liquid influent means having an output pressure capability greater than an expected vapor pressure of said liquid hydrocarbon;

a liquid effluent line connected to a portion of said separation chamber which is below said liquid level in said separation chamber, said liquid effluent line having effluent pump means responsive to said liquid level sensing means for maintaining a constant liquid level in said separation chamber;

a gas effluent line connected to a portion of said separation chamber which is above said liquid level in said separation chamber; and means for controlling separation chamber pressure at a selected substantially constant value within a range of pressure values, said range having a first endpoint below atmospheric pressure and a second endpoint above atmospheric pressure;

b) flowing a liquid hydrocarbon through said separation chamber while maintaining a constant liquid level therein;

c) adjusting separation chamber temperature to a selected temperature; and d) directly measuring separation chamber pressure with said pressure sensor means under substantially constant liquid level and separation chamber temperature conditions, said separation chamber pressure under said level and pressure conditions equal to the vapor pressure of said liquid hydrocarbon.

13. A method for continuous generation of a liquid hydrocarbon having a desired vapor pressure, comprising the steps of:

a) providing an apparatus comprising:

a separation chamber having temperature sensor means, liquid level sensing means, and pressure sensor means therein, said separation chamber further having a heating element in thermal communication therewith, said heating element responsive to an output signal from said temperature sensor means;

selectable flow liquid influent means connected to a portion of said separation chamber which is above a liquid level in said separation chamber, said selectable flow liquid influent means having an output pressure capability greater than an expected vapor pressure of said liquid hydrocarbon;

a liquid effluent line connected to a portion of said separation chamber which is below said liquid level in said separation chamber, said liquid effluent line having effluent pump means responsive to said liquid level sensing means for maintaining a constant liquid level in said separation chamber;

a gas effluent line connected to a portion of said separation chamber which is above said liquid level in said separation chamber;

means for controlling separation chamber pressure at a selected constant value within a range of pressure values, said range having a first endpoint below atmospheric pressure and a second endpoint above atmospheric pressure;

manifold means connected to said liquid influent line, said manifold means comprising a plurality of liquid inlet lines combining to a single discharge into said liquid influent line, each of said liquid inlet lines connected to a different liquid hydrocarbon source;

b) successively flowing a liquid hydrocarbon from each of said liquid hydrocarbon sources through said separation chamber at a current temperature of said liquid hydrocarbon while maintaining constant liquid level in said separation chamber, said control valve closed preventing any gas effluent flow from said separation chamber;

c) measuring a vapor pressure for each of said liquid hydrocarbons equivalent to the pressure in said separation chamber;

d) determining a ratio of flow rates of said different liquid hydrocarbon sources at said current temperature that yields a desired vapor pressure of a resulting mixture of different liquid hydrocarbons; and e) combining said liquid hydrocarbon sources at the determined ratio to yield a liquid hydrocarbon effluent having a vapor pressure equal to said desired vapor pressure.

14. A method of determining a gas-oil ratio of a liquid hydrocarbon comprising the steps of:

a) providing an apparatus comprising:

a separation chamber having temperature sensor means, liquid level sensing means, and pressure sensor means therein, said separation chamber further having a heating element in thermal communication therewith, said heating element responsive to an output signal from said temperature sensor means;

selectable flow liquid influent means connected to a portion of said separation chamber which is above a liquid level in said separation chamber, said selectable flow liquid influent means having an output pressure capability greater than an expected vapor pressure of said liquid hydrocarbon;

a liquid effluent line connected to a portion of said separation chamber which is below said liquid level in said separation chamber, said liquid effluent line having effluent pump means responsive to said liquid level sensing means for maintaining a constant liquid level in said separation chamber;

a gas effluent line connected to a portion of said separation chamber which is above said liquid level in said separation chamber; and pressure control means connected to said separation chamber, said pressure control means responsive to said pressure sensor means for maintaining said separation chamber at a selected pressure in a range below and above atmospheric pressure;

b) flowing a liquid hydrocarbon through said separation chamber at a desired separation chamber temperature and liquid level;

c) measuring a gas effluent rate and a liquid hydrocarbon effluent rate;

d) determining a gas-oil ratio of said liquid hydrocarbon by dividing said gas effluent rate by said liquid hydrocarbon effluent rate.

15. A method of determining shrinkage of a liquid hydrocarbon comprising the steps of:

a) providing an apparatus comprising:

a separation chamber having temperature sensor means, liquid level sensing means, and pressure sensor means therein, said separation chamber further having a heating element in thermal communication therewith, said heating element responsive to an output signal from said temperature sensor means;

selectable flow liquid influent means connected to a portion of said separation chamber which is above a liquid level in said separation chamber, said selectable flow liquid influent means having an output pressure capability greater than an expected vapor pressure of said liquid hydrocarbon;

a liquid effluent line connected to a portion of said separation chamber which is below said liquid level in said separation chamber, said liquid effluent line having effluent pump means responsive to said liquid level sensing means for maintaining a constant liquid level in said separation chamber;

a gas effluent line connected to a portion of said separation chamber which is above said liquid level in said separation chamber; and pressure control means connected to said separation chamber, said pressure control means responsive to said pressure sensor means for maintaining said separation chamber at a selected pressure in a range below and above atmospheric pressure;

b) flowing a liquid hydrocarbon through said separation chamber at a desired separation chamber temperature and liquid level;

c) measuring a liquid hydrocarbon influent rate and a liquid hydrocarbon effluent rate;

d) determining a liquid hydrocarbon shrinkage by dividing said liquid hydrocarbon effluent rate by said liquid hydrocarbon effluent rate.

16. A method for determining a vapor pressure of a liquid hydrocarbon comprising the steps of:

a) providing an apparatus comprising:

a separation chamber having temperature sensor means, liquid level sensing means, and pressure sensor means therein, said separation chamber further having a heating element in thermal communication therewith, said heating element responsive to an output signal from said temperature sensor means;

selectable flow liquid influent means connected to a portion of said separation chamber which is above a liquid level in said separation chamber, said selectable flow liquid influent means having an output pressure capability greater than an expected vapor pressure of said liquid hydrocarbon;

a liquid effluent line connected to a portion of said separation chamber which is below said liquid level in said separation chamber, said liquid effluent line having effluent pump means responsive to said liquid level sensing means for maintaining a constant liquid level in said separation chamber;

a gas effluent line connected to a portion of said separation chamber which is above said liquid level in said separation chamber; and pressure control means connected to said separation chamber, said pressure control means responsive to said pressure sensor means for maintaining said separation chamber at a selected pressure in a range below and above atmospheric pressure;

b) creating a pressure within said separation chamber lower than an expected vapor pressure of a liquid hydrocarbon;

c) closing said gas effluent line;

d) adjusting said pressure control means to permit a maximum separation chamber pressure greater than a maximum output pressure of said selectable flow liquid influent means;

e) flowing said liquid hydrocarbon through said separation chamber at a substantially constant separation chamber temperature and liquid level;

f) recording said separation chamber pressure with time-, said separation chamber pressure with time values defining a curve;

g) determining a vapor pressure of said liquid hydrocarbon equal to the pressure of an asymptote to said curve.

* * * * *